United States Patent [19]

Nakagawa

[11] Patent Number: 5,956,146
[45] Date of Patent: Sep. 21, 1999

[54] BIREFRINGENCE MEASURING APPARATUS FOR OPTICAL DISC SUBSTRATE

[75] Inventor: Eiji Nakagawa, Yokosuka, Japan

[73] Assignee: Victor Company of Japan, Ltd., Yokohama, Japan

[21] Appl. No.: 09/014,740

[22] Filed: Jan. 28, 1998

[30] Foreign Application Priority Data

Jan. 29, 1997 [JP] Japan .................................. 9-029534

[51] Int. Cl.$^6$ ....................................................... G01J 4/00
[52] U.S. Cl. ........................................ 356/365; 356/376
[58] Field of Search ................................ 356/365; 1/376

[56] References Cited

U.S. PATENT DOCUMENTS

| | | | |
|---|---|---|---|
| 4,655,589 | 4/1987 | Cestaro et al. | 356/365 |
| 5,305,090 | 4/1994 | Kowalski | 356/365 |
| 5,341,205 | 8/1994 | McLandrich et al. . | |
| 5,517,022 | 5/1996 | Bock et al. . | |

FOREIGN PATENT DOCUMENTS

| | | |
|---|---|---|
| 2-304729 | 12/1990 | Japan . |
| 3-218440 | 9/1991 | Japan . |
| 07229828 | 8/1995 | Japan . |
| 7-229828 | 8/1995 | Japan . |

OTHER PUBLICATIONS

Goodman et al, "Temperature Dependence of the Birefringence of Optical–disk Substrates", Applied Optics, vol. 35, No. 16, Jun. 1996, pp. 3031–3038, XP000594923.

Shribak, "Autocollimating Detectors of Birefringence", SPIE, vol. 2782, 1996, pp. 805–813, XP002065162.

*Primary Examiner*—Frank G. Font
*Assistant Examiner*—Reginald A. Ratliff
*Attorney, Agent, or Firm*—Michael N. Meller

[57] ABSTRACT

A birefringence measuring apparatus 30 measures a birefringence of a transparent substrate D1 of an optical disc D having a reflective layer D2 thereon by detecting a reflected light beam L2, which is a reflection of a light beam L1 from the disc. The light beam irradiates the disc at an incident angle of "α", penetrates the transparent substrate, and reflected by the reflective layer. The light beam emitted from a light source 1 has a coherence length shorter than an optical path length P which is a sum of optical paths P1 and P2. The optical path P1 is a distance from the surface of the transparent substrate to the reflective layer, and the optical path P2 is a distance from the reflective layer to the surface of the transparent substrate.

3 Claims, 2 Drawing Sheets

BIREFRINGENCE MEASURING APPARATUS FOR OPTICAL DISC SUBSTRATE

BACKGROUND OF THE INVENTION

1. Field of the Invention

The present invention relates to a measuring apparatus for an optical disc, and particularly relates to a birefringence measuring apparatus for an optical disc substrate.

2. Description of the Prior Art

Some kind of resin, such as polycarbonate, is mainly used for a transparent substrate of an optical disc. An optical anisotropy, namely, birefringence of a molded transparent substrate is caused by an injection molding process because a direction and a speed of flow of a melted resin are fluctuated when the resin is injected from a center of a mold of the optical disc to a periphery thereof. Thus, the birefringence of the transparent substrate of the optical disc fluctuates along a radial direction of the optical disc, and does not fluctuate along a circumferential direction thereof.

Accordingly, it is required to select only a transparent disc having small birefringence which is allowable for an optical disc by evaluating the birefringence thereof after molding. A read only memory (ROM) type optical disc has a series of pits as a spiral information track formed thereon, and a reflective layer and a protective layer are formed successively thereon. A random access memory (RAM) type optical disc has a spiral groove thereon, and a memory layer, a reflective layer, and a protective layer are formed successively thereon.

Birefringence measuring methods are categorized into a transmission method and a reflection method.

The transmission method detects the birefringence of the transparent substrate having no reflective layer by using a laser beam which irradiates the transparent substrate vertically, and by detecting a transmitted light. The transmission method can measure precisely the birefringence of single transparent substrate having no reflective layer, but it cannot measure that of an adhered optical discs having a reflective layer.

The reflection method can measure the birefringence of an optical disc having a reflective layer. In this method, the laser beam penetrates the transparent substrate slantingly and is reflected by the reflective layer. An analyzer is revolved around an axis of a reflected laser beam, and a photodetector measures an intensity of the reflected laser beam. Then the birefringence of the optical disc is computed by utilizing a measured value of the polarization of the reflected laser beam.

In a prior art, a laser for emitting the laser beam is a HeNe gas laser or a single-mode laser diode, both of which have the laser beams of large coherence length.

In the reflection method, there are two reflections, one is a reflection from a surface of the transparent substrate, another is a reflection from the reflective layer of the optical disc. These two reflections easily interfere with each other, as the laser beam of the laser which is used in the prior art has a large coherence length. A photodetector detects these interfered reflections, which are changed in their intensities periodically by interference.

The interference is determined by amplitude and phase differences between the two reflections. The amplitude of the reflection from the surface of the transparent substrate is introduced by utilizing a refractive index of the transparent substrate, and that of the reflection from the reflective layer of the optical disc is introduced by using refractive indices of the reflective layer and of the transparent substrate. The difference of phase between the two reflections is determined by the thickness of the transparent substrate.

A wavelength of the laser beam used in this reflection method is in the range of several hundreds in nm. When the thickness accuracy of the transparent substrate is made in the order of nm over the whole area thereof, the interference caused by the two reflections can be estimated precisely in theory. But, actually, it is very difficult to know the thickness of the transparent substrate precisely in the accuracy of nm where the measurement is performed. Moreover, the thickness of the transparent substrate is about 0.6 mm for example, and irregularity of the thickness thereof is generally larger than several μm, which is much larger than the wavelength of the laser beam. Thus, a value of the interference of the two reflections may change depending on the measured portion thereof, and cannot be estimated precisely. Accordingly, the birefringence measuring method of the prior art, which is forced to use interfered reflections, has a difficulty of removing the variable amplitude associated to the interfered reflections caused by the two reflections from the detected light beams. Therefore, the birefringence of the transparent substrate cannot be measured accurately.

As mentioned before, the ideal measurement of the birefringence is to irradiate the transparent substrate vertically. But, this measurement cannot be applied to the adhered optical disc, because beam axes of a light source and a reflected light are common to each other, and the light source and the photodetector cannot be positioned at the same axis. In this arrangement for measuring the birefringence, it is obliged to increase the incident angle of the laser beam from the vertical axis, so as to keep away the axes of the laser beam from the reflected beam.

In the birefringence measurement of the reflection method mentioned above, two reflections of which one is from the surface of the transparent substrate and another is from the reflective layer of the optical disc, interfere with each other. To avoid the interference of the two reflections, a beam radius of the laser has to be small, or the angle of the axis of the laser beam with respect to the disc surface has to be large. When the laser beam is formed as a parallel ray, the beam radius thereof is generally a few mm, and it is difficult to make it smaller. The birefringence strongly depends on the angle of the axis of the laser beam with respect to the disc surface, therefore, it is difficult to estimate the birefringence of vertical incidence from that of large angle. Therefore, it is difficult to measure accurately the birefringence of the transparent substrate of the optical disc by the birefringence measurement of the reflection method of the prior art.

SUMMARY OF THE INVENTION

Accordingly, a general object of the present invention is to provide a birefringence measuring apparatus which can measure a birefringence of a transparent substrate of an optical disc accurately by using an optical source which can avoid reflections to interfere each other, that is, one reflection from the surface of the transparent substrate and another reflection from a reflective layer of the optical disc.

Another object of the present invention is to provide a birefringence measuring apparatus for measuring a birefringence of a transparent substrate of an optical disc having the transparent substrate and a reflective layer comprised of a light beam emitting device for emitting a light beam and irradiating at a predetermined incident angle the transparent substrate of an optical disc disposed in predetermined position thereof and comprised of the reflective layer laminated on the transparent substrate, wherein the light beam penetrates the transparent substrate and is reflected from the reflective layer for measuring a birefringence of the transparent substrate, and wherein the light beam has a coherence length being smaller than an optical path length of the light beam defined by sum of distances; a distance from the surface of the transparent substrate to the reflective layer and another distance from the reflective layer to the surface of the transparent substrate.

Further and another object of the present invention is to provide a birefringence measuring apparatus mentioned above of another object, wherein the light beam emitting device is a semiconductor laser having a characteristics of multi-mode oscillation.

Still another object of the present invention is to provide a birefringence measuring apparatus, wherein the light beam emitting device is a semiconductor laser having a characteristics of single-mode oscillation and is driven by a drive current on which a high frequency signal is superimposed.

DETAILED DESCRIPTION OF THE PREFERRED EMBODIMENTS

The present invention will now be described in detail with reference to the accompanying drawings.

A birefringence measuring apparatus of the present invention uses a reflective method, and is characterized by using a light beam emitting device having a coherence length which is shorter than an optical path length defined by a sum of a length from a surface of a transparent substrate of an optical disc to a reflective layer thereof and another length from the reflective layer to the surface of the transparent substrate. In this method, a birefringence of the transparent substrate thereof is measured precisely, as no interference occurs in the measuring process.

Figure 1:
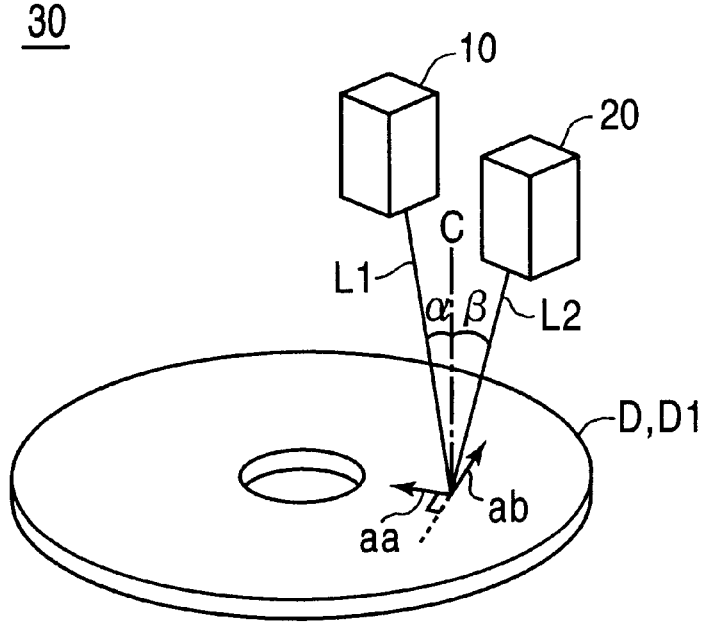
FIG. 1 shows a schematic and perspective view of a birefringence measuring apparatus of the present invention for measuring a birefringence of an optical disc.

FIG. 1 shows a schematic and perspective view of a birefringence measuring apparatus of the present invention for measuring a birefringence of an optical disc.

Figure 2:
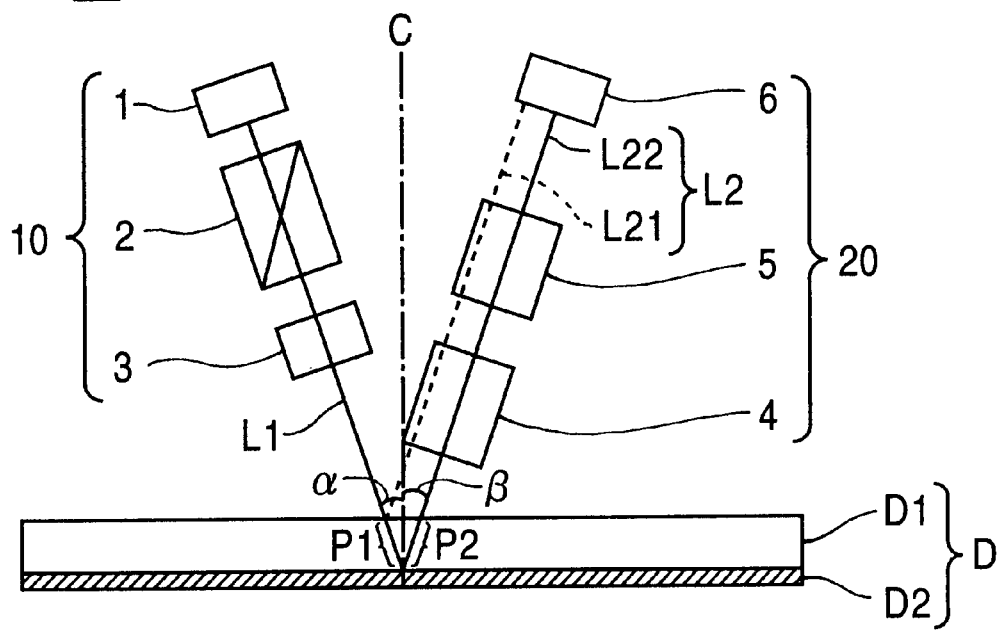
FIG. 2 shows a side view of the birefringence measuring apparatus shown in FIG. 1.

FIG. 2 shows a side view of the birefringence measuring apparatus shown in FIG. 1.

Figure 3:
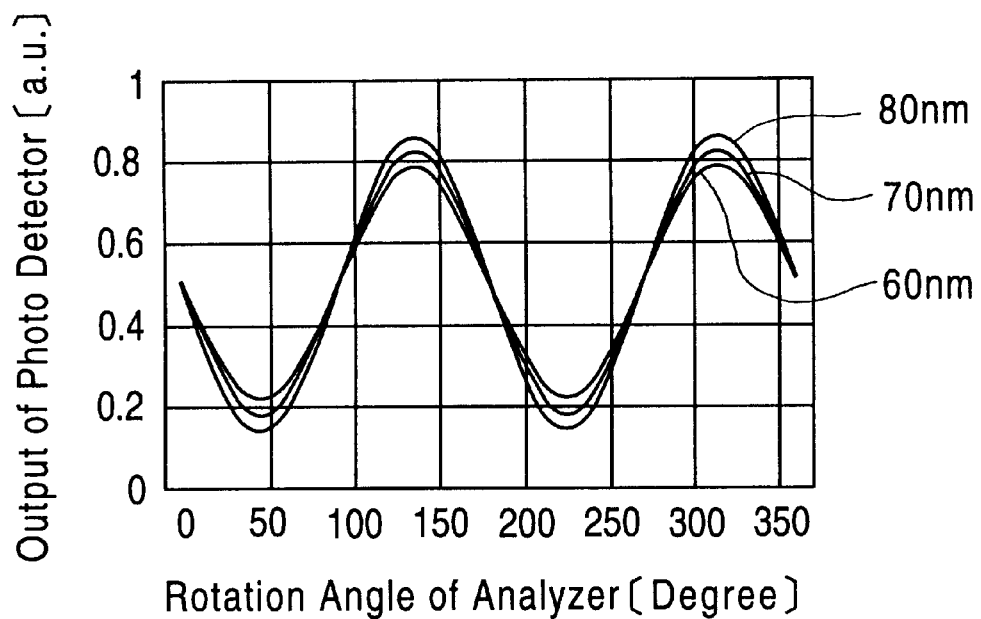
FIG. 3 shows an idealized output signal of a photodetector of the birefringence measuring apparatus shown in FIG. 2.

FIG. 3 shows an idealized output signal of a photodetector of the birefringence measuring apparatus shown in FIG. 2.

Figure 4:
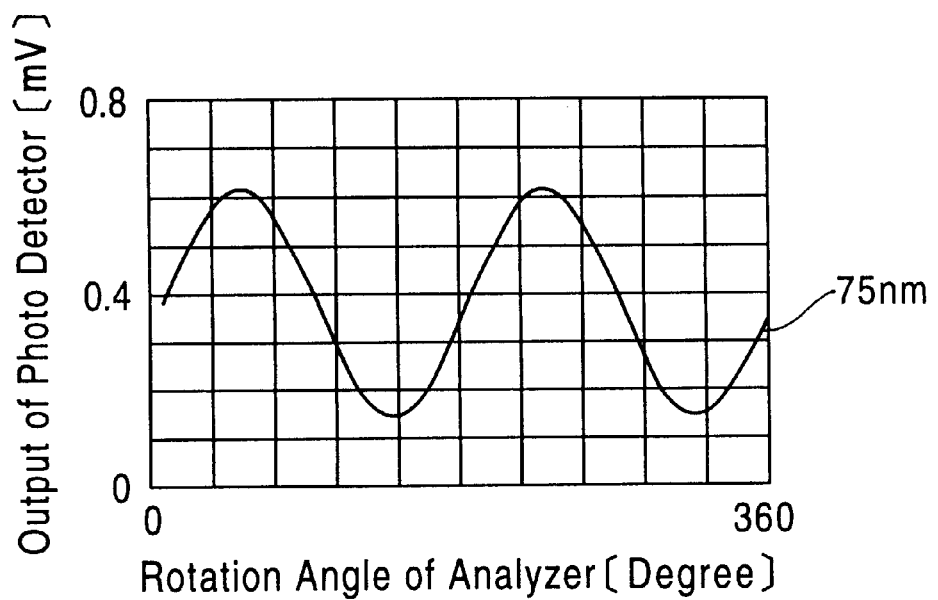
FIG. 4 shows an actual output signal of a photodetector of the birefringence measuring apparatus of the present invention.

FIG. 4 shows an actual output signal of a photodetector of the birefringence measuring apparatus of the present invention.

As shown in FIGS. 1 and 2, a birefringence measuring apparatus 30 of the present invention has a light emitting device 10 and a light detecting device 20 on both sides of the line "c" perpendicular to the surface of the transparent substrate D1 of the optical disc D. When the position of the light detecting device 20 is fixed, the light emitting device 10 may be moved in the direction of "aa" (radial direction) or "ab" (circumference direction) for searching its optimum position.

The light emitting device 10 emits a light beam L1 and irradiates the surface of the transparent substrate D1 at a incident angle "α". A part of the light beam L1 is reflected from the surface of the transparent substrate D1, which is a first reflected light beam L21 of a reflection angle "β". The reflection angle "β" is equal to the incident angle "α". Another part of the light beam L1 penetrates the transparent substrate D1 and reflected by a reflective layer D2, which is a second reflected light beam L22 and includes a birefringence component developed in the transparent substrate D1. Thus, a reflected light beam L2 including the first and second reflected light beams L21 and L22 is incident on the light detecting device 20.

As shown in FIG. 2, the light emitting device 10 is comprised of a light source 1, a polarizer 2, and a quarter-wave plate 3. The detecting device 20 is comprised of an analyzer 4, a condenser lens 5, and a photodetector 6.

The light source 1 emits the light beam L1 for measurement whose coherence length is smaller than an optical path length P which is the sum of optical path lengths P1 and P2, wherein a path length P1 is a travelling distance of the light beam L1 from the surface of the transparent substrate D1 to the reflective layer D2, and the path length P2 is a travelling distance of the second reflected light beam L22 from the reflective layer D2 to the surface of the transparent substrate D1.

The birefringence measuring apparatus 30 of the present invention is based on the following theory.

When two light beams having amplitudes "$a_1$" and "$a_2$" are added together, an added light amplitude I is given by $$I = a_1^2 + a_2^2 + 2a_1 \times a_2 \times \cos \Delta \qquad \text{eq. 1}$$

a1: an amplitude of the first reflected light beam a2: an amplitude of the second reflected light beam Δ: a phase difference between the first and the second reflected light beams As known from this eq. 1, a variation of the added light amplitude I is $\pm 2a_1 \times a_2$ depending on the phase difference Δ.

Generally, the transparent substrate D1 is made of polycarbonate, and made by an injection molding. Therefore, it is difficult to control the irregularity of the thickness of the transparent substrate D1 in the order of the optical wavelength. Accordingly, an interference term of the eq. 1, which is shown as $2a_1 \times a_2 \times \cos \Delta$, varies randomly. When the interference term of the eq. 1 is negligible, the added light amplitude I is expressed by an addition of the 2nd power of the amplitude of the first reflected light beam and that of the amplitude of the second reflected light beam, namely, $a_1^2 + a_2^2$. A feature of the present invention is to reduce the effect of the interference term of the eq. 1 by setting the coherence length of the light beam L1 being smaller than the optical path length P.

An operation of the birefringence measuring apparatus 30 of the present invention will be explained in the following.

The light beam L1 emitted from the light source 1 and penetrating the polarizer 2 and the quarter-wave plate 3, is changed to a circularly polarized light, and irradiates the transparent substrate of the optical disc D. A part of the light beam L1 is reflected from the surface of the transparent substrate D1 and becomes the first reflected light beam L21. Another part of the light beam L1 penetrates the transparent substrate D1 and reflected from the reflective layer D2, and becomes the second reflected light beam L22 which is changed to an elliptically polarized light by an effect of the birefringence of the transparent substrate D1. Thus, the reflected light beam L2, which is the sum of the first and second reflected light beams L21 and L22, passes through the analyzer 4 and the condenser lens 5, and irradiates the photodetector 6.

For measuring the intensity of the reflected light beam L2, the output of the photodetector 6 is measured as the analyzer 4 is revolved 360° around the axis of the reflected light beam L2, and the photodetector 6 measures the intensity of the reflected light beam L2. Since there is no interference between the first and second reflected light beams L21 and L22, the first reflected light beam L21 can be calculated by measuring a refractive index of the surface of the transparent substrate D1. The intensity of the second reflected light beam L22 is obtained by subtracting the intensity of the first reflected light beam L21 from the intensity of the reflected light beam L2. The intensity of the second reflected light beam L22 varies as the analyzer 4 is revolved, and maximum $I_{max}$ and minimum $I_{min}$ thereof are obtained. Here, the birefringence "br" of the transparent substrate is given by, $$br = \frac{\lambda}{2\pi}\left\{\cos^{-1}\left(\frac{2}{\frac{I_{min}}{I_{max}}+1}-1\right) - \frac{\pi}{2}\right\} \qquad \text{eq. 2}$$

Exemplary, the incident angle α of the light beam L1 is 7 degrees, and a diameter of the light beam L1 is about 1 mm. The thickness of the transparent substrate D1 is 0.6 mm. The first reflected light beam L21 and the second reflected light beam L22 are added together and form the reflected light beam L2.

An output of the analyzer 4 which rotates indicates a vibrating locus of the electric vector of the elliptically polarized light.

The locus of the electric vector of the elliptically polarized light is given by, $$\left(\frac{E_x}{a_x}\right)^2 + \left(\frac{E_y}{a_y}\right)^2 - 2\frac{E_x E_y}{a_x a_y}\cos\Delta = \sin^2\Delta \qquad \text{eq. 3}$$

$a_x$: an amplitude of the electric vector $E_x$
$a_y$: an amplitude of the electric vector $E_y$ In the birefringence measuring apparatus 30 of the present invention, the light beam L1 is selected to have a characteristic of $a_x=a_y$. When $a_x$ and $a_y$ are equal to 1, the eq. 3 is given by, $$E_x^2+E_y^2-2 E_x E_y \cos\Delta=\sin^2\Delta \qquad \text{eq. 4}$$

The eq. 4 expresses an ellipse which touches internally to a square having a side length of 2. A long axis "a" and a short axis "b" are given by, $$a^2+b^2=2 \qquad \text{eq. 5}$$

When the birefringence of the transparent substrate D1 is measured by the birefringence measuring apparatus 30 of the present invention, the sum of $I_{max}$ and $I_{min}$ is constant, as $I_{max}$ is "$a^2$", and $I_{min}$ is "$b^2$". This is introduced by eq. 5. This means that the peak value of the output of the photodetector 6 is constant, which means that the birefringence thereof is obtained precisely.

FIG. 3 shows a calculation result of the output of the photodetector 6 responding to the reflected light beam L2 from three sampled points on the disc D, which have respectively different birefringence values. Here, the interference term is idealized to be zero.

In FIG. 3, the abscissa is the rotation angle of the analyzer 4, and the ordinate is the output of the photodetector 6. FIG. 3 shows calculated results of outputs from the photodetector 6, derived according to the equation 2. As can be seen from the figure, respective detector outputs in relation to the birefringence of 60 nm, 70 nm, and 80 nm exhibits no difference in their DC components caused otherwise by the interference between the first and the second reflected light beams L21 and L22, as the interference term is intentionally set to zero. Accordingly, though peak values of the detector output curves differ from each other, the fundamental levels thereof are the same.

The birefringence measuring apparatus 30 can measure the birefringence of an optical disc accurately even if there is a thickness irregularity of the transparent substrate, and the reason is mentioned in the following.

The birefringence measurement is conducted by using a multi-mode semiconductor laser emitting a mixture of various wavelengths and having a coherence length of 1 mm as the light source 1. When the thickness of the transparent substrate D1 is 0.6 mm, the optical path length P is about 1.9 mm, which is derived from that the thickness of the transparent substrate D1 is doubled and multiplied by the refractive index of 1.58 thereof. Thus, the coherence length of 1 mm is apparently smaller than the optical path length P of 1.9 mm. Therefore, the first and the second reflected light beams L21 and L22 do not interfere each other. Then, the reflected light beam L2 detected by the photodetector 6 is simply the sum of the first and second reflected light beams L21 and L22. The second reflected light beam L22, which has an information of birefringence of the transparent substrate D1 and is necessary for calculating the birefringence, is obtained by subtracting the first reflected light beam L21 from the reflected light beam L2, as the first reflected light beam L21 can be calculated by measuring a refractive index of the surface of the transparent substrate D1. Thus, the accurate value of the birefringence of the transparent substrate D1 is obtained.

The oscillation of the single-mode semiconductor laser can be changed to a multi-mode oscillation by superimposing a high frequency signal of about 400 MHz to a drive current therefor. By this method, the coherence length of the light beam L1 emitted from the single-mode semiconductor laser becomes smaller than the optical path length P of 1.9 mm. Accordingly, there occurs no interference between the first and the second reflected light beams L21 and L22. Thus, the birefringence of the transparent substrate D1 is measured precisely.

In FIG. 4, the birefringence of the transparent substrate D1 was actually measured in three times changing measuring positions on the optical disc along a circumference thereof, using the birefringence measuring apparatus 30 of the present invention. In FIG. 4, three sinusoidal detector outputs representing measured birefringence agree with each other to form one curve. The birefringence value thereof was calculated therefrom as 75 nm. It is proved that the measurement is accurate, despite that there are differences in thickness of the optical disc in respective measured positions thereof, as there is no interference between the first and the second reflected light beams L21 and L22. Thus, an accurate measurement of the birefringence was performed by the improvement made on the light source 1.

According to the birefringence measuring apparatus 30 of the present invention, by employing the light source having a coherence length which is shorter than the sum of the path length from the surface of the transparent substrate to the reflective layer and another path length from the reflective layer to the surface of the transparent substrate, the adverse effect of the interference between the first and second reflected light beams caused in the birefringence measurement of reflective method of the prior art, is eliminated. Even when the reflection occurs at the surface of the transparent substrate, the birefringence property thereof is precisely measured by the birefringence measuring apparatus 30 of the present invention.

What is claimed is:

1. A birefringence measuring apparatus for measuring a birefringence of a transparent substrate of an optical disc having the transparent substrate and a reflective layer laminated on said transparent substrate comprising:

a light source for emitting an optical beam, said optical beam irradiating said transparent substrate and passing through said transparent substrate at a predetermined angle and being reflected by said reflective layer and passing again through said transparent substrate, wherein said optical beam has a coherence length shorter than a sum of a first optical path from a surface of said transparent substrate to said reflective layer and a second optical path from said reflective layer to said surface of said transparent substrate.

2. A birefringence measuring apparatus claimed in claim 1, wherein said light source is a multi-mode semiconductor laser.

3. A birefringence measuring apparatus claimed in claim 1, wherein said light source is a single-mode semiconductor laser and is driven by a current containing a high frequency signal.

* * * * *